United States Patent [19]
Stephan

[11] 3,975,542
[45] Aug. 17, 1976

[54] ETHYL- AND VINYLBENZENES AS ANTITHROMOBIOTIC AGENTS

[75] Inventor: Erwin A. Stephan, Indianapolis, Ind.

[73] Assignee: Eli Lilly and Company, Indianapolis, Ind.

[22] Filed: May 15, 1975

[21] Appl. No.: 577,975

Related U.S. Application Data

[63] Continuation-in-part of Ser. No. 485,876, July 5, 1974, abandoned.

[52] U.S. Cl. .............................. 424/353; 424/340; 424/356
[51] Int. Cl.² ............... A61K 31/03; A61K 31/015; A61K 31/085
[58] Field of Search ................................. 424/353

[56] References Cited
OTHER PUBLICATIONS

Derwent Farmdoz, 43879V124 Abst. German, 2,259,243 (6-6-74).

Derwent Farmdoz, 43879V/24 Abst. Belgian, 808,147 (6-4-74).

Derwent Farmdoz, 4379V/24 Abst. Netherlands, 7,316,503 (6-6-74).

Derwent Farmdoz, 43879V/24 Abst. French, 2,208,673 (8-2-76).

*Primary Examiner*—Stanley J. Friedman
*Attorney, Agent, or Firm*—William E. Maycock; Everet F. Smith

[57] ABSTRACT

A method of treating vascular thrombosis in warmblooded animals, employing an ethyl- or vinylbenzene as the active antithrombotic agent.

14 Claims, No Drawings

ETHYL- AND VINYLBENZENES AS ANTITHROMOBIOTIC AGENTS

CROSS-REFERENCED TO RELATED APPLICATION CROSS-REFERENCE

This application is a continuation-in-part of application Ser. No. 485,876, filed 5 July 1974, now abandoned.

BACKGROUND OF THE INVENTION

This invention relates to a method of treating vascular thrombosis in warm-blooded animals, employing an ethyl- or vinylbenzene as the active antithrombotic agent.

A thrombus generally is defined as an obstruction, formed from components of blood, within the vascular system. When a thrombus is either free-floating in the blood stream or has been removed by the blood stream to a new location, it is referred to as an embolus. Thrombosis, which refers to the formation, development, or presence of a thrombus, is responsible for a variety of disorders which generally are termed thromboembolic diseases. Such diseases include phlebothrombosis, thrombophlebitis, pulmonary embolism, retinal thrombosis, myocardial infarction, and cerebral infarction, among others. More generally, such diseases can be considered to result from a vascular thrombosis, i.e., a thrombus within the vascular system of the body.

The chemoprophylactic or chemotherapeutic management of thromboembolic diseases generally involves compounds which fall into one of three categories: (1) platelet aggregation inhibitors, (2) anticoagulants, and (3) fibrinolytic agents. The chemotherapeutic use of fibrinolytic agents is based upon the fact that fibrin frequently forms the primary structural support of a thrombus. Dissolution of the fibrin should result in lysis of the thrombus, with restoration of blood flow. Anticoagulants and platelet aggregation inhibitors, on the other hand, generally are employed prophylactically. Anticoagulants are more effective in the treatment of venous thrombosis than arterial thrombosis. The successful prophylaxis of arterial thrombosis must deal with the etiologic role of the platelet. The value of platelet function inhibitors in venous thrombosis, on the other hand, will be reflected by the extent to which platelets are involved in the formation of those thrombi. In any event, there are within the circulatory system regions of stasis in which fibrin formation would be virtually the sole factor in thrombosis, and other regions of high hemodynamic activity where the platelet nidus alone could block the vessel.

Consequently, the search for effective new platelet aggregation inhibitors continues to be an important research activity.

Certain ethyl- and vinylbenzenes, defined hereinafter, now have been discovered to be active antithrombotic agents, even though many of such compounds are known.

SUMMARY OF THE INVENTION

In accordance with the present invention, a method of treating vascular thrombosis in warm-blooded animals is provided which comprises administering to a warm-blooded animal in need of such treatment an amount effective for treating vascular thrombosis of an ethyl- or vinylbenzene having the following general formula:

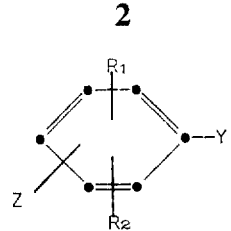

wherein Y is a monovalent group which is either ethyl or vinyl; $R_1$ and $R_2$ are monovalent groups independently selected from the group consisting of hydrogen, halo, $C_1$–$C_3$ alkyl, and $C_1$–$C_3$ alkoxy; and Z is either a monovalent group which is $C_5$–$C_7$ cycloalkyl, with the proviso that at least one of $R_1$ and $R_2$ must be other than hydrogen, or a group of the formula

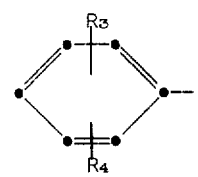

wherein $R_3$ and $R_4$ are monovalent groups independently selected from the group consisting of hydrogen, halo, $C_1$–$C_3$ alkyl, and $C_1$–$C_3$ alkoxy, with the proviso that at least one of $R_1$, $R_2$, $R_3$, and $R_4$ must be other than hydrogen.

DETAILED DESCRIPTION OF THE INVENTION

As used herein, the term "treatment" is meant to include both active treatment and preventive or prophylactic treatment. Additionally, the term "halo" is meant to include fluoro, chloro, bromo, and iodo.

According to the method of the present invention, vascular thrombosis in a warm-blooded animal is treated by administering to a warm-blooded animal in need of such treatment an amount effective for treating vascular thrombosis of an ethyl- or vinylbenzene as defined hereinbefore. Such compound can be administered parenterally or enterally, and preferably orally. The compound normally will be administered at a dosage level sufficient to provide a concentration of the compound in the blood of from about 1 to about 250 μg/ml, and preferably from about 1 to about 100 μg/ml. On the average, such concentration is approximately equivalent to a dose of from about 0.05 to about 20 mg/kg, with the preferred concentration being approximately equivalent to a dose of from about 0.05 to about 10 mg/kg. The necessary concentration in the blood can be achieved by administering a single dose or up to about six smaller doses per day, depending upon the tolerance of the patient to the compound, persistence of the compound in the blood stream, and other factors. When dosage is oral, the range of administration of such compound normally will be from about 1 to about 150 mg/kg.

Preferably, such compound is employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate, and stearic acid.

Such a composition can be formulated as tablets or enclosed in capsules for convenient administration. The compound also can be mixed with a liquid and administered as an elixir, suspension, or the like. In the case of parenteral administration, the compound is conveniently formulated in saline to constitute an injectable liquid solution. Other adjuvants and modes of administration are known to those skilled in the art.

Suitable pharmaceutical carriers are described in E. W. Martin, et al., "Remington's Pharmaceutical Sciences," 14th Ed., Mack Publishing Company, Easton, Pa., 1965.

The activities of the ethyl- and vinylbenzenes relative to parenteral administration were demonstrated by the procedure of R. G. Herrmann, et. al., Proc. Soc. Exp. Biol. Med., 135, 100 (1970), and references cited therein. The activities of such compounds relative to oral administration were demonstrated by the procedure of R. G. Herrmann, et al., ibid., 139, 548 (1972). By either procedure, the ethyl- and vinylbenzenes described hereinbefore were found to provide at least about 20 percent inhibition of platelet aggregation.

Examples of ethyl- and vinylbenzenes suitable for use in the method of the present invention include, among others:

3-chloro-4-cyclohexyl-1-ethylbenzene,
1-ethyl-4-(2-fluorophenyl)benzene,
1-ethyl-3-(3-fluorophenyl)benzene,
4-(2-chlorophenyl)-1-ethylbenzene,
1-ethyl-4-(2,4-difluorophenyl)benzene,
1-ethyl-2-(3,5-difluorophenyl)benzene,
1-ethyl-4-(2,5-difluorophenyl)benzene,
1-ethyl-4-(2,6-difluorophenyl)benzene,
1-ethyl-4-(2-methylphenyl)benzene,
1-ethyl-2-(3-methylphenyl)benzene,
1-ethyl-4-(2-methoxyphenyl)benzene,
1-ethyl-3-fluoro-4-phenylbenzene,
1-ethyl-4-fluoro-3-phenylbenzene,
2-chloro-1-ethyl-4-phenylbenzene,
1-ethyl-3-methoxy-4-phenylbenzene,
1-ethyl-5-methoxy-2-phenylbenzene,
1-ethyl-3-fluoro-4-(2-fluorophenyl)benzene,
1-ethyl-3-(2-fluorophenyl)-5-methoxybenzene,
4-cyclohexyl-3-fluoro-1-vinylbenzene,
4-(2-fluorophenyl)-1-vinylbenzene,
3-(2,5-difluorophenyl)-1-vinylbenzene,
4-(3,5-difluorophenyl)-1-vinylbenzene,
2-(2,6-difluorophenyl)-1-vinylbenzene,
4-(2,6-difluorophenyl)-1-vinylbenzene,
4-(2-methylphenyl)-1-vinylbenzene,
3-(2-methoxyphenyl)-1-vinylbenzene,
2-fluoro-4-phenyl-1-vinylbenzene,
4-chloro-3-phenyl-1-vinylbenzene,
3-methoxy-4-phenyl-1-vinylbenzene, and
3-fluoro-4-(2-fluorophenyl)-1-vinylbenzene.

The preferred ethyl- and vinylbenzenes are those compounds wherein Z in the general formula defined hereinbefore is the group,

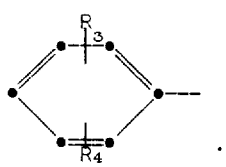

Examples of such preferred compounds include, among others:

1-ethyl-4-(2-fluorophenyl)benzene,
4-(2-chlorophenyl)-1-ethylbenzene,
1-ethyl-3-methoxy-4-phenylbenzene,
1-ethyl-4-(3-fluorophenyl)benzene,
1-ethyl-4-(2-methylphenyl)benzene,
1-ethyl-4-(2,4-difluorophenyl)benzene,
1-ethyl-4-(2,5-difluorophenyl)benzene,
1-ethyl-4-(2,6-difluorophenyl)benzene,
1-ethyl-3-fluoro-4-(2-fluorophenyl)benzene,
4-(2-fluorophenyl)-1-vinylbenzene,
4-(2-chlorophenyl)-1-vinylbenzene,
3-methoxy-4-phenyl-1-vinylbenzene,
4-(3-fluorophenyl)-1-vinylbenzene,
4-(2-methylphenyl)-1-vinylbenzene,
4-(2,4-difluorophenyl)-1-vinylbenzene,
4-(2,5-difluorophenyl)-1-vinylbenzene,
4-(2,6-difluorophenyl)-1-vinylbenzene, and
3-fluoro-4-(2-fluorophenyl)-1-vinylbenzene.

A most preferred group of ethyl- and vinylbenzenes are those compounds wherein Z is the group,

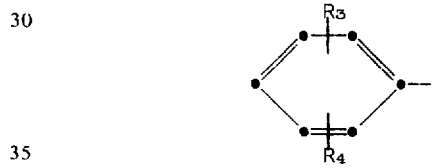

and $R_1$, $R_2$, $R_3$, and $R_4$ independently are hydrogen or halo with at least one of $R_1$, $R_2$, $R_3$, and $R_4$ being halo. The preferred halo groups are fluoro and chloro. Examples of such compounds have been listed hereinabove.

The ethyl- and vinylbenzenes which can be employed in the method of the present invention are prepared by known methods from the corresponding acetophenones; ethyl-, vinyl-, and ethynylbenzenes; benzaldehydes; phenyl methyl carbinols; and the like. Such intermediates are readily prepared by known methods, usually from the appropriate cycloalkyl- and phenylbenzenes. The cycloalkyl- and phenylbenzenes in turn are readily prepared by known methods.

It will be apparent to one skilled in the art that all of the ethyl- and vinylbenzenes suitable for use in the method of the present invention cannot be prepared by any one procedure or reaction scheme. However, the limitations inherent in any given procedure are well understood by one skilled in the art, and such limitations can be avoided either by appropriate molecular manipulations or by the use of alternative synthetic procedures.

The present invention is further described, but not limited, by the following examples which illustrate preferred procedures for the preparation of the ethyl- and vinylbenzenes to be employed in the method of the present invention. All temperatures are in degrees centigrade.

EXAMPLE 1

Preparation of 1-ethyl-4-(2-fluorophenyl)benzene.

1-Ethynyl-4-(2-fluorophenyl)benzene, 22 g, was reduced in a Parr Instrument Company Series 3910 Low Pressure Shaker-type Apparatus, using 100 ml of benzene, 2 g of five percent palladium on charcoal, and 0.5 ml of concentrated sulfuric acid. Reduction was carried out at room temperature and at an initial hydrogen pressure of 50 psig. Within 15 minutes, the hydrogen pressure had dropped to 32 psig. Hydrogen pressure was increased to 52 psig and agitation continued for two hours, with no additional hydrogen pressure drop. The reaction mixture was filtered and the filtrate was neutralized with two percent aqueous sodium carbonate. The resulting mixture was washed with water. The benzene phase was separated, dried over anhydrous sodium sulfate, and filtered. The benzene was evaporated and the residue was vacuum distilled to give 17 g of 1-ethyl-4-(2-fluorophenyl)benzene, bp 99°–101°/0.3 mm. The following elemental analysis was obtained:

Calculated for $C_{14}H_{13}F$: C, 83.97; H, 6.54; F, 9.49
Found: C, 84.23; H, 6.39; F, 9.42.

EXAMPLE 2

Preparation of 1-ethyl-4-(4-fluorophenyl)benzene.

The procedure of Example 1 was repeated, except that the 1-ethynyl-4-(2-fluorophenyl)benzene was replaced with 1.5 g of 1-ethynyl-4-(4-fluorophenyl)benzene, the amount of catalyst was reduced to 0.5 g, the sulfuric acid was omitted, initial hydrogen pressure was 48 psig, and the reduction was allowed to proceed overnight. Evaporation of the benzene left a solid which was recrystallized from hexane to give 1-ethyl-4-(4-fluorophenyl)benzene, mp 60°–63°. The following elemental analysis was obtained:

Calculated for $C_{14}H_{13}F$: C, 83.97; H, 6.54; F, 9.49
Found: C, 84.02; H, 6.35; F, 9.37.

EXAMPLE 3

Preparation of 1-ethyl-4-(2-chlorophenyl)benzene

The procedure of Example 1 was repeated, except that the 1-ethynyl-4-(2-fluorophenyl)benzene was replaced with 23.1 g of 4'-(2-chlorophenyl)acetophenone, the amount of benzene was increased to 150 ml, the amount of catalyst was increased to 3 g, the amount of sulfuric acid was increased to 2 ml, and the reduction was allowed to proceed for 13 hours. Evaporation of the benzene left a residue which was vacuum distilled to give 14 g of 1-ethyl-4-(2-chlorophenyl)benzene, bp 110°–112°/0.4 mm. The following elemental analysis was obtained:

Calculated for $C_{14}H_{13}Cl$: C, 77.59; H, 6.05; Cl, 16.36
Found: C, 77.79; H, 5.79; Cl, 16.18.

EXAMPLE 4

Preparation of 1-ethyl-4-(4-chlorophenyl)benzene

The procedure of Example 3 was repeated, except that the 4'-(2-chlorophenyl)acetophenone was replaced with an equal amount of 4'-(4-chlorophenyl)acetophenone, the amount of benzene employed was increased to 200 ml, and the amount of sulfuric was reduced to 5 drops. After seven hours, hydrogen pressure had dropped to 35.5 psig. Evaporation of the benzene left a solid which, according to nuclear magnetic resonance analysis, contained only about 67 percent of the desired ethylbenzene. Consequently, the solid was subjected to the hydrogenation procedure again, using 200 ml of benzene, 2 g of catalyst, and 1 ml of concentrated sulfuric acid. The solid obtained upon evaporation of the benzene was recrystallized from hexane, giving 1-ethyl-4-(4-chlorophenyl)benzene, mp 103°–127 104°. The following elemental analysis was obtained:

Calculated for $C_{14}H_{13}Cl$: C, 77.59; H, 6.05; Cl, 16.36
Found: C, 77.80; H, 5.98; Cl, 16.17.

EXAMPLE 5

Preparation of 4-(2-fluorophenyl)-1-vinylbenzene.

1-Ethynyl-4-(2-fluorophenyl)benzene, 29.6 g, was reduced in a Parr Instrument Company Series 3910 Low-Pressure Shaker-Type Apparatus, using 450 ml of pyridine, and 0.3 g of five percent palladium on barium sulfate; reduction was carried out at room temperature for 30 minutes and at an initial hydrogen pressure of 30 psig. The reaction mixture was filtered and the filtrate was evaporated in vacuo. The residue was vacuum distilled to give 20.5 g of solid which was recrystallized from methanol to give 4-(2-fluorophenyl)-1-vinylbenzene, mp 38°. The material contained traces of pyridine and 1-ethyl-4-(2-fluorophenyl)benzene, as shown by nuclear magnetic resonance analysis. The following elemental analysis was obtained:

Calculated for $C_{14}H_{11}F$: C, 84.82; H, 5.59; F, 9.58
Found: C, 84.49; H, 4.54; F, 9.23.

As pointed out hereinbefore, the treatment of vascular thrombosis by the method of the present invention, and by antithrombotic agents in general, largely is prophylactic in nature. Such prophylaxis comprises the administration of an antithrombotic agent to an individual based upon a need of the individual for such administration. In general, an individual will have a need for treatment with antithrombotic agents under either of two situations: (1) the individual already has suffered overt manifestations of a thromboembolic disease, or (2) an individual has an identifiable risk of contracting a thromboembolic disease but has not yet shown any overt manifestations of such disease. In either case, the prophylactic treatment of the individual with an antithrombotic agent is intended to prevent thromboembolic disease in the individual or, at least, to minimize the effects of such disease upon the health of the individual should such disease occur.

What is claimed is:

1. A method of treating vascular thrombosis in warm-blooded animals which comprises administering to a warm-blooded animal in need of such treatment an amount effective for treating vascular thrombosis of a compound of the formula,

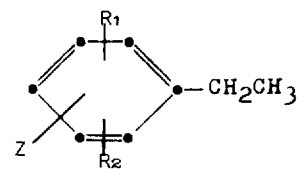

wherein $R_1$ and $R_2$ are monovalent groups independently selected from the group consisting of hydrogen, halo, $C_1$–$C_3$ alkyl, and $C_1$–$C_3$ alkoxy, and Z is either a monovalent group which is $C_5$–$C_7$ cycloalkyl, with the proviso that at least one of $R_1$ and $R_2$ must be halo, or a group of the formula

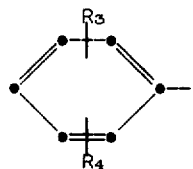

wherein $R_3$ and $R_4$ are monovalent groups independently selected from the group consisting of hydrogen, halo, $C_1$–$C_3$ alkyl, and $C_1$–$C_3$ alkoxy, with the proviso that at least one of $R_1$, $R_2$; $R_3$, and $R_4$ must be halo.

2. The method of claim 1, wherein such compound is administered at a level of from about 0.05 to about 150 mg./kg. of animal body weight.

3. The method of claim 1, wherein Z is the group of the formula,

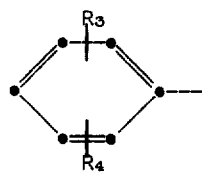

4. The method of claim 1, wherein Z is the group of the formula,

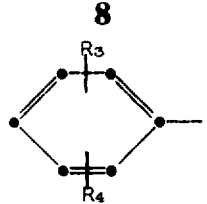

and $R_1$, $R_2$, $R_3$, and $R_4$ independently are hydrogen or halo.

5. The method of claim 4, wherein $R_1$, $R_2$, $R_3$, and $R_4$ independently are selected from the group consisting of hydrogen, fluoro, and chloro.

6. The method of claim 5, wherein three of $R_1$, $R_2$, $R_3$, and $R_4$ are hydrogen.

7. The method of claim 5, wherein the compound is 1-ethyl-4-(2-fluorophenyl)benzene.

8. The method of claim 5, wherein the compound is 4-(2-chlorophenyl)-1-ethylbenzene.

9. The method of claim 5, wherein the compound is 1-ethyl-4-(3-fluorophenyl)benzene.

10. The method of claim 5, wherein two of $R_1$, $R_2$, $R_3$, and $R_4$ are hydrogen.

11. The method of claim 5, wherein the compound is 1-ethyl-4-(2,4-difluorophenyl)benzene.

12. The method of claim 5, wherein the compound is 1-ethyl-4-(2,5-difluorophenyl)benzene.

13. The method of claim 5, wherein the compound is 1-ethyl-4-(2,6-difluorophenyl)benzene.

14. The method of claim 5, wherein the compound is 1-ethyl-3-fluoro-4-(2-fluorophenyl)benzene.

* * * * *